(12) United States Patent
Provot et al.

(10) Patent No.: US 6,605,435 B1
(45) Date of Patent: Aug. 12, 2003

(54) METHOD FOR AMPLIFYING ALL OF THE DNA FRAGMENTS IN A SAMPLE, INCLUDING SMALL AND DAMAGED FRAGMENTS, BY PRETREATING THE FRAGMENTS WITH P1 NUCLEASE

(75) Inventors: Christian Provot, Le Cendre (FR); Franck Chaubron, Chamalieres (FR); Anne-Céline Martin, Chamalieres (FR)

(73) Assignee: Genolife, Gerzat (FR)

( * ) Notice: Subject to any disclaimer, the term of this patent is extended or adjusted under 35 U.S.C. 154(b) by 0 days.

(21) Appl. No.: 09/786,193

(22) PCT Filed: Sep. 6, 1999

(86) PCT No.: PCT/FR99/02113

§ 371 (c)(1),
(2), (4) Date: Mar. 2, 2001

(87) PCT Pub. No.: WO00/14277

PCT Pub. Date: Mar. 16, 2000

(30) Foreign Application Priority Data

Sep. 4, 1998 (FR) .............................................. 98 11081

(51) Int. Cl.[7] .............................. C12Q 1/68; C12P 19/34
(52) U.S. Cl. ........................... 435/6; 435/91.1; 435/91.2
(58) Field of Search ........................... 435/6, 91.1, 91.2

(56) References Cited

U.S. PATENT DOCUMENTS

| 5,162,209 A | | 11/1992 | Scheele ...................... 435/91.2 |
| 6,114,149 A | * | 9/2000 | Fry et al. .................... 435/91.2 |

FOREIGN PATENT DOCUMENTS

| EP | 0 778 351 | | 6/1997 | |
| WO | 90/01065 | * | 2/1990 | ........... C12P/19/34 |
| WO | WO 95 11995 | | 5/1995 | |
| WO | WO 97 08185 | | 3/1997 | |
| WO | WO 97 27317 | | 7/1997 | |

OTHER PUBLICATIONS

Toellner, et al., "The use of reverse transcription polymerase chain reaction to analyse large numbers of mRNA species from a single cell", *J. Immunol. Methods,* (1996) 191:71–75.
International Search Report for corresponding PCT application No. PCT/FR99/02113.
Wexler, et al.; "A procedure to amplify cDNA from dsRNA templates using the polymerase chain reaction"; *Methods in Molecular and Cellular Biology,* vol. 2 (1991) pp. 273–379.
Cormack, et al.; "Rapid amplification of genomic ends (RAGE) as a simple method to clone flanking genomic DNA" *Gene*: vol. 194, No. 2, pp. 273–276.
Janssen, et al.; "Evaluation of the DNA fingerprinting method AFLP as a new tool in bacterial taxonomy" *Microbiology,* vol. 142, No. 142 (Jul. 1996), pp. 1881–1893.
Sedlak, B.J.; "Gene chip technology ready to impact diagnostic markets," *Genetic Engineering News,* Dec. 1, 1997, p. 1, 14, 34.

* cited by examiner

*Primary Examiner*—Kenneth R. Horlick
(74) *Attorney, Agent, or Firm*—Finnegan, Henderson, Farabow, Garrett & Dunner, L.L.P.

(57) ABSTRACT

A method of amplifying all of the DNA fragments of a sample, including fragments that are small or damaged, comprises an initial step of generating free 3'-OH end with P1 nuclease. The method also provides for extraction of the DNA fragments from a sample and reduction of their size to between 100 and 300 base pairs. A poly(dX) oligonucleotide is added to the 3' ends of the DNA fragments using a terminal transferase, and the DNA is denatured and hybridized to a poly(dY) primer complementary to the poly(dX) ends. Finally, the DNA is polymerized with DNA polymerase. The resulting DNA can be amplified by denaturing and slowly renaturing the complementary strands.

23 Claims, 6 Drawing Sheets

Figure 1A:
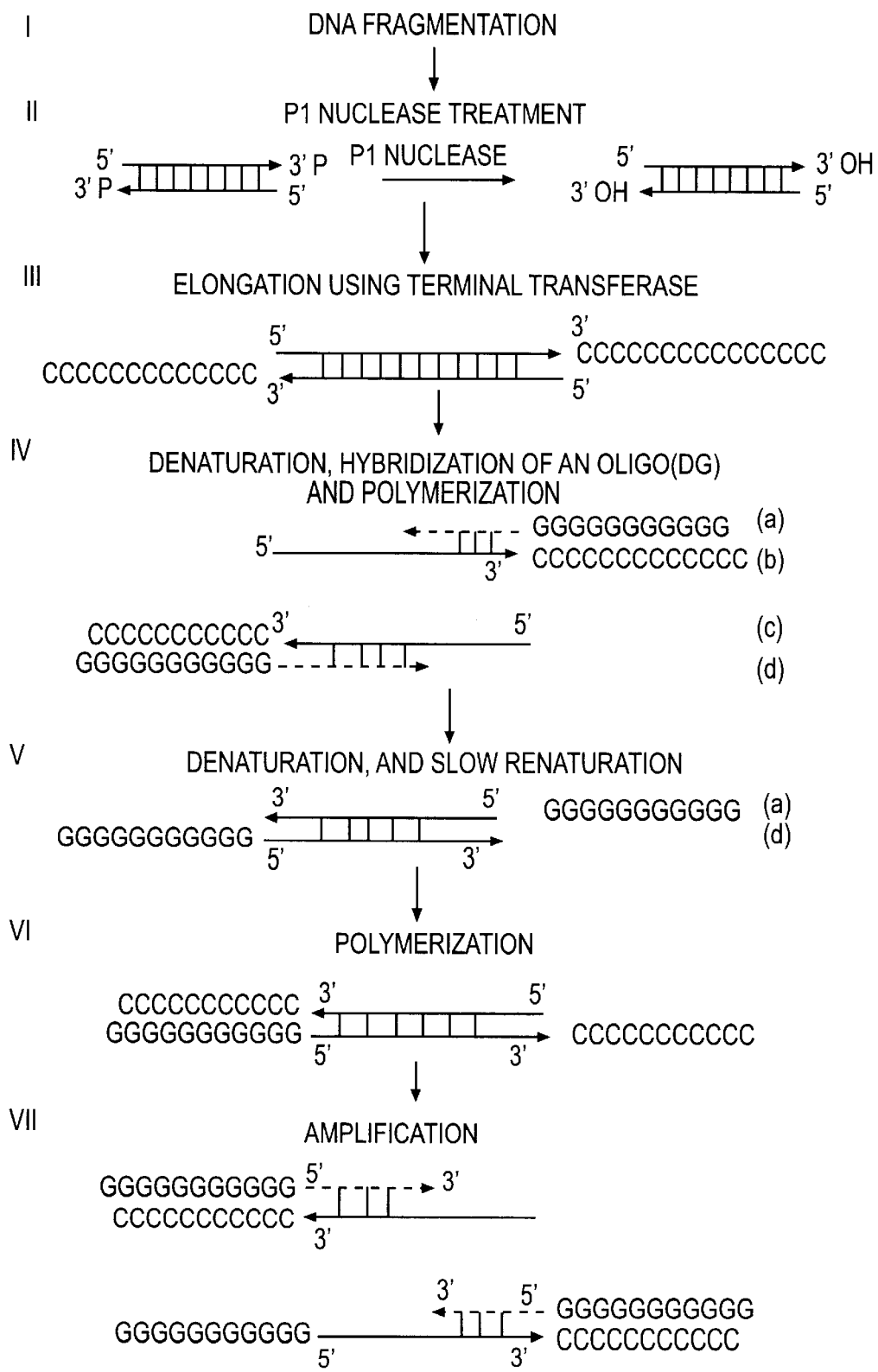

METHOD FOR AMPLIFYING ALL OF THE DNA FRAGMENTS IN A SAMPLE, INCLUDING SMALL AND DAMAGED FRAGMENTS, BY PRETREATING THE FRAGMENTS WITH P1 NUCLEASE

The present invention relates to a method for characterizing all of the DNA fragments in a sample, said fragments being small in size and often being damaged and/or in trace amounts, in particular in finished or transformed products. The invention is based on the pre-amplification of all of the DNA fragments before an optional specific amplification and, therefore, the method is particularly suitable for the analysis, by molecular hybridization, in particular on DNA chips, of all of the DNA originating from any type of sample, possibly highly complex and/or having undergone denaturing treatments.

Various methods for characterizing a sample which is complex from a biochemical point of view, based on the identification of nucleotide sequences, are used in particular in the agro-foods domain. These methods can be applied to raw materials, such as a simple grain, however, they show certain limitations with regard to the analysis of a product containing many elements forming part of its composition and/or having undergone treatments which denature the molecules to be characterized. It is therefore necessary to enrich and/or to purify the material contained in a sample of interest if it contains treated or conditioned constituents originating from various origins, as is the case for finished products.

Once the nucleic acid material has been obtained, to a degree of purity sufficient to allow its analysis, it must be subjected to one or more tests intended to characterize it by molecular hybridization. However, these methods are generally restricted to analytical laboratories, because of either the use of radioactivity (although methods such as luminescence are tending to replace radioactivity), or the number of samples able to be analyzed simultaneously being too small. In certain cases, these techniques cannot be used because of a lack of sensitivity, this lack being essentially due to the low amount, and/or to the poor quality, of the nucleic acid material recovered from the sample.

The most commonly used technique is the PCR (Polymerase Chain Reaction). This method makes it possible to amplify specifically, in the course of many reaction cycles (of the order of 25 to 45), a nucleic acid included between two primers specific for known nucleotide sequences. These primers are oligonucleotides of the order of 15 to 40 bases, the sequence of which matches perfectly with the flanking sequences of the sequence to be amplified. It is conventional, using one nucleic acid sample, to amplify only one sequence.

"Multiplex" PCRs have been described in [Apostolakos (1993) Anal Biochem, 213, 277–284]. Under specific conditions, it is possible, in the same reaction tube, to amplify several sequences simultaneously using several pairs of primers. The number of pairs of primers rarely exceeds 3. Specifically, above this number, the amplifications lose their specificity (appearance of unexpected amplification products) or one or more amplifications does (do) not function, or barely function(s), although an example of the multiplex amplification of 9 sequences has been described [Edwards (1994) PCR Methods Applic., 3, S65–S75].

Other techniques, more or less derived from PCR, have been developed

LCR (Ligase Chain Reaction), based on the use of a heat-stable DNA ligase [Barany (1991) Proc. Natl Acad Sci USA, 88, 189–193].

Gap-LCR is derived from LCR.

ERA (End Run Amplification) is developed by Beckman Instruments, its derivative being GERA (Gap-ERA) [Adams (1994) Novel amplification technologies for DNA/RNA-based diagnostics meeting, San Francisco, Calif., USA].

CPR (Cycling Probe Reaction), which uses a DNA-RNADNA chimera and ribonuclease H [Duck (1990) BioTechniques, 9, 142–147], and is developed by the company ID Biochemical Corporation.

SDA (Strand Displacement Amplification) [Walker (1992) Nucleic Acids Res., 20, 1691–1696], patented by the company Becton Dickinson, which allows multiplex analysis [Walker (1994) Nucleic Acids Res., 22, 2670–2677]. However, it is difficult to analyze more than 3 sequences simultaneously by this method.

TAS (Transcription-based Amplification) [Kwoh (1989) Proc. Natl Acad Sci. USA, 86, 1173–1177], uses reverse transcriptase and T7 polymerase. Self Sustained Sequence Replication is related to TAS [Gingeras (1990) Ann. Biol Clin., 48, 498–501].

NASBA (Nucleic Acid Sequence-Based Amplification) is quite similar to 3 SR [Kievits (1991) J Virol Methods, 35, 273–286].

Finally, the properties of the $Q\beta$ replicase (RNA dependent-RNA polymerase isolated from the $Q\beta$ bacteriophage) were brought to light before PCR [Haruna (1965) Proc Natl. Acad. Sci USA, 54, 579–587], and this enzyme was used in amplification techniques, from 1983 [Miele (1983) J Mol. Biol, 171, 281 295].

In view of the documents cited above, it appears that it is not possible to characterize hundreds, and even more so thousands, of nucleotide sequences contained in a solution of DNA, in a restricted number of steps.

It is, however, possible to amplify, in a limited number of steps and using a considerable number of primers (greater than the number used in multiplex), virtually all of the DNA contained in an extract.

One of the approaches might be the AFLP (Amplified Restriction Fragment Polymorphism or Amplified Fragment Length Polymorphism) technique, which consists in using restriction enzymes to digest the DNA at specific sites, and then linkers which are attached specifically to these cleavage sites, and which also provide a DNA sequence sufficient to then allow the hybridization of primers. In a method sold, for example, by the company Gibco-BRL, the EcoRI and MseI enzymes are used, and then 8 linkers/primers for each cleavage site are used for the amplification step.

This method is, however, restricted to the analysis of DNA of quite good quality (generally directly extracted from a tissue or from an organism). Specifically, in order for the amplifications to take place, the two linkers must be present at the ends of the digested DNA, and therefore the DNA must have been digested at these sites. In the case of DNA derived from a transformed product, the size of this DNA is of the order of a few hundred base pairs (200 to 400). The probability of the presence of an EcoRI site (EcoRI recognizing a site composed of the 6-base pair palindrome; GAATTC) is $\frac{1}{4}^6$, i.e. one potential site per 4096 base pairs.

Restriction enzymes which recognize the most common sites (4 base pairs), such as MseI, will, on the other hand, statistically cleave the DNA every 256 base pairs. Since it is necessary to cleave the DNA twice in order to generate the two PCR priming sites, the probability of generating these two sites on a fragment of a few hundred base pairs is low, and the amplification products do not reflect all of the starting DNA.

Short repeated sequences, dispersed throughout the length of the genome, termed "microsatellites", have been used to amplify, with the aid of primers complementary to these microsatellite sequences, the sequences included between them [Zietkeiwicz (1994) Genomics, 20, 176 183; Weising (1995) PCR Methods Applic., 4, 249–255]. This type of amplification makes it possible especially to carry out genetic typing, "fingerprinting", based on a qualitative analysis of the amplification products [Thomas (1993) Theor Appl Genet 86, 985–990]. A large proportion of the genome can thus be amplified, but not all of it, in particular because certain microsatellite sequences are too far apart to allow PCR amplification.

Three methods have been described, claiming the non-specific amplification of all the nucleotide sequences of a sample [Ludecke (1989) Nature, 338, 348–350 or Kinzler (1989) Nucleic Acids Res, 17, 3645–3653, Zhang (1992) Proc Natl Acad; USA, 89, 5847–5851; and Grothues (1993) Nucleic Acids Res, 21, 1321–1322, and U.S. Pat. No. 5,731,171].

The principle of this latter method, which is drawn from the two others and which claims a technical improvement, is based on the use of a very large number of oligonucleotides of 10 to 20 bases, representing all possible sequences, to which a specific sequence is associated in 3'. In the course of a first PCR, with a small number of cycles, these oligonucleotides will theoretically pair with all the sequences, and the amplification cycles will incorporate the specific sequence into all the fragments amplified. After gel filtration, the aim of which is to separate the free oligonucleotides from the DNA, a second PCR using an oligonucleotide complementary to the specific sequence is performed on the DNA. According to the authors, this method allows the amplification of all of the DNA, on samples containing sizes ranging from 400 base pairs to 40 megabases. However, the oligonucleotides which can hybridize to all the possible sequences, on the same DNA strand, do not necessarily hybridize to the ends, and therefore the entire fragment is not amplified. In addition, the hybridization temperature is 30° C. with regard to the first PCR with these random oligonucleotides (temperature below which it is difficult to drop with PCR machines). Since the temperature of hybridization of an oligonucleotide is calculated on the basis of 2° C. per A or T, and of 4° C. per G or C, an oligonucleotide consisting of a combination of 10 A or T hybridizes at 20° C. and, therefore, will not hybridize, or will hybridize very poorly, at 30° C.: When using such a temperature, the sequence of the oligonucleotide should not be more than 50% A/T-rich. This problem is, moreover, raised in that publication, which specifies, in addition, that a number of sequences are at the very least under-represented and therefore, implicitly, that certain sequences are not amplified. The risk of amplifying a specific sequence only partially increases in a manner which is inversely proportional to the amount of this sequence in the starting medium, and the appearance of false negatives is a problem for the reliable analysis of a sample.

The amplification of the total mRNAs of cells has been described in particular from page 120 to 121 of "La PCR, un procédé de réplication in vitro" [PCR, in vitro replication method], Daniel Larzul, Collection Génie Génétique [Genetic Engineering Collection], Ed Lavoisier. This method benefits from the fact that the majority of mRNAs have a poly(A) tail at the 3' end. A poly(dT) oligonucleotide is used as a primer in the first amplification step, and then a poly(dG) is added to the 3' end of the newly synthesized strand, using terminal transferase, and is used as an anchoring site for a poly(dC) primer.

Although the amplification of the total mRNAs has certain characteristics which are quite similar to the present invention, this technique is not a priori directly applicable for accomplishing the objective of the present invention. Specifically, after denaturing the strands obtained by elongation using poly(dC), taq DNA polymerase is allowed to act, with a poly(dG) primer. Two products are thus obtained, which cannot be amplified since two new poly(dC) primers would have a 3'–5' polarity, which cannot be used as a substrate for the polymerases. The method according to the invention makes it possible to overcome this difficulty, in particular by carrying out slow denaturation/renaturation, which allows the two 5'-poly (dG)-sequence to be amplified-3' strands to anneal, or using a second step implementing a terminal transferase. The polymerase synthesizes poly(dC) ends which are then used to anchor the poly(dg) primers, which this time have the correct 5'3' polarity. However, the technique of the invention is only valid for amplifying relatively small strands. It can, moreover, be pointed out that the techniques described in U.S. Pat. No. 5,162,209 and WO 97/08185, based on the fact that the MRNA naturally possesses a poly(A) tail, cannot be used as a starting point for a PCR amplification, since said techniques, which are intended more for cloning, do not produce products which can be amplified.

The detection of DNA product amplified, by PCR or other methods, generally uses electrophoretic analysis. Methods for detection in 96-well microplates have also been described. The PCR amplification product is denatured and hybridized in a microplate well to which is attached a capture oligonucleotide [Running (1990) BioTechniques, 8, 276–277] or a single-stranded DNA containing a capture sequence [Kawai (1993) Anal Biochem, 209, 63–69]. One at least of the primers used in the PCR is, for example, biotinylated, and the detection of the hybridization is carried out by adding streptavidin coupled to an enzyme such as peroxidase, and then a chromogenic substrate for the enzyme.

Commercially available variants of this assay use other forms of detection, such as fluorescence. Using a capture oligonucleotide attached to the wells, a biotinylated PCR primer and an internal amplification standard, it has even been possible to carry out quantitative PCR [Berndt (1995) Anal. Biochem., 225, 252–257]. The technique of capturing amplified DNA products is not restricted to PCR since it has, for example, been adapted by the company Applied Biosystems, to the detection of Microbacterium tuberculosis by LCR [Winn-Deen (1993) Mol. Cell. Probes, 7, 179 186].

These methods, whether quantitative or not, provide information, using a PCR, only on the presence or absence of a target DNA sequence at the start. One variant makes it possible, using a single PCR on the HLA-DR locus, to identify, semiautomatically, 30 different typings through the use of 20 capture oligonucleotide probes and 2 detection probes coupled to peroxidase [Cros (1992) Lancet, 340, 870–873]. A similar assay, also used for HLA typing, is sold by the company Perkin Elmer.

In parallel to the use of microplates, DNA chips, intended to identify DNA sequences, have been described and sold. The principle of this technique consists in identifying nucleic acid (DNA or RNA) sequences in a sample, based on molecular hybridization. The chip carries, grafted onto a suitable surface, hundreds or thousands of oligonucleotides of interest. The DNA of the sample is denatured and placed under conditions for hybridization with the chip.

However, two main constraints appear in this method
(1) it must be possible to detect the hybridization phenomenon,
(2) the amount of DNA hybridized must satisfy the constraints of the sensitivity of the detection system.

In order to satisfy the first constraint, the DNA is generally labeled using a fluorescent marker. The GENFET detection system must, however, be cited as an alternative. It is a device the composition of which is close to that of a field effect transistor (FET) developed in the "laboratoire de physico-chimie des interfaces [laboratory of physicochemistry of interfaces] (Ecole Centrale, Lyons, France). In this case, the hybridization leads to modification of the charge density of the semi-conductor at the interface of the semi-conductor at the Si and $SiO_2$ interface, this modification being measured.

In order to satisfy the second constraint, the NA of the sample is generally amplified by PCR. In this case, the use of amplification primers coupled, for example, to a fluorescent label, or the incorporation of one or more fluorescent nucleotide(s), satisfies both constraints simultaneously. However, the advantage of the chip lies in its capacity to supply, from one DNA sample, hundreds or thousands of items of information. The search for point mutations is a good example thereof. An amplification product is hybridized on a chip comprising many nucleotide capture sequences contained in the amplified fragment, each capture sequence differing by one base. It is thus possible, under the hybridization conditions for which only the entirely complementary sequence amplification products hybridize, to determine, according to the capture sequences hybridized, the sequence of the amplification product, and to deduce therefrom the presence of a possible mutation with respect to a reference allele.

The chip is therefore of great value since the general scheme of the experiment is: preparation of DNA—amplification—hybridization on the chip. In this scheme, the analysis of the "DNA chip" step relates to a single DNA amplification (with a single set of primers) since all the capture probes carried by the chip have the same amplification product as a target.

If the intention is to design a chip carrying capture probes having multiple amplification products as targets, it will be necessary either to use the AFLP or microsatellite techniques (or a derived technique) to amplify all of the genomic DNA, or to carry out multiple amplifications, which, because of the high number of manipulations upstream of the "chip" step, makes its value as a high throughput screening or characterization tool relatively nonadvantageous. Overall amplification of the DNA of a sample, of AFLP type, would a priori be compatible with the screening possibilities of the chip. Now, AFLP is not suitable for the amplification of small DNA fragments contained in a complex sample such as agro-food finished products.

Consequently, the method according to the invention allows the characterization of all of the DNA fragments of a sample, said fragments being small in size and often being damaged and/or in trace amounts, in particular in finished or transformed products, or when samples are taken in various places. In addition, the method of the present invention, which is valid for DNA which is small in size, can also be applied to DNA which is large in size, and the size of which can be reduced. The advantage provided by the invention lies in the pre-amplification of all of the DNA fragments before an optional specific amplification and, therefore, the method is particularly suitable for the analysis, by molecular hybridization, in particular on DNA chips, of all the DNA originating from any type of sample, possibly considerably complex and/or having undergone denaturing treatments.

Thus, no document of the prior art describes or suggests the present invention as defined hereinafter.

DESCRIPTION OF THE INVENTION

The present invention relates to a method for amplifying all of the DNA fragments of a sample, comprising the following steps:

a) extraction of the DNA and reduction, where appropriate, of the size of the DNA fragments extracted, by physical or enzymatic cleavage so as to obtain a mean length of between approximately 25 and 500 bp.

b) addition of a poly(dX) oligonucleotide to the 3' ends of the DNA fragments using a terminal transferase.

c) denaturation and annealing with a poly(dY) primer complementary to the poly(dx) of step b).

d) synthesis using a DNA polymerase in the presence of the four dNTPs.

The samples according to the invention can originate from any source, from any product, material or substance, in unmodified form or which has undergone treatments, transformations and/or conditioning. With regard to a new sample the condition of which is not known in advance, the experimenter can, according to his/her preference, choose a technique for analyzing DNA fragment lengths, from all the methods commonly used in the technical field.

The expression "where appropriate" is intended to mean a situation in which the fragments extracted from a sample have conserved a quite considerable size (approximately greater than 500 bp, on average). It is then necessary to reduce the size of the fragments. This situation can occur when nontransformed raw materials are analyzed.

In the context of the invention, the expression "poly(dX)", "poly(dX) homopolymer" or "poly(dX) oligonucleotide" is intended to mean an oligonucleotide 11 to 15 nucleotides long, X referring to one of the nucleotides dG, dC, dA or dT, said nucleotide possibly being chemically modified. This sequence can optionally comprise one or two random nucleotides at its 3' end. The expression "poly(dY)" is intended to mean a sequence comprising at least one repeat of any base, said sequence being complementary to poly(dX).

Advantageously, the method described above benefits from a step e) allowing the production of a DNA which can be amplified by PCR. Step e) consists of denaturation and then of slow renaturation in order to anneal the complementary strands synthesized in step d) carrying protruding poly(dy) ends. The slow renaturation is carried out by dropping from a temperature of between 85° C. and 105° C. to a temperature of between 45° and 25° C., preferably from 95° C. to 35° C., with a temperature ramp ranging approximately from 0.5° C. to 0.05° C. per second, preferably of 0.2° C. per second. This slow renaturation allows re-annealing of the DNA strands and the formation of DNA molecules which can be amplified by PCR.

An alternative which is equivalent to the slow renaturation consists of a second terminal transferase step carried out under the same conditions as step b). This makes it possible to have a DNA with a poly(dx) homopolymeric sequence at the two ends of the DNA. This DNA is subjected to denaturation and then hybridization with a poly(dY) and polymerization of the complementary strand in the presence of a DNA polymerase.

The DNA obtained in step e) can then be amplified with the following steps:
  f) synthesis, using a DNA polymerase, of the poly(dX)s complementary to said protrusions, optionally in the presence only of dXTP.
  g) series of PCR-type cycles consisting of denaturation, annealing of the poly(dY) primer and synthesis using a DNA polymerase.

In the method of the invention, it is advantageous to amplify DNA fragments which have a mean length of between 100 and 300 bp, preferably equal to 200 bp.

The addition of a poly(dx) oligonucleotide to the 3' ends of said DNA fragments, as mentioned in step c), is carried out preferably using a terminal transferase. Before this addition of a poly(dX) oligonucleotide to the 3' ends, free 3'-OH ends can be generated using the P1 nuclease. Similarly, it is possible to label the poly(dx) or poly(dY) oligonucleotide radioactively, with a fluorescent or luminescent group, or using a system allowing revelation by colorimetry, in particular the system biotin-streptavidin coupled to an enzyme which reacts with a chromogenic, fluorigenic or luminescent substrate (for example peroxidase). Another solution may consist in incorporating, during one of the synthesis steps, at least one labeled nucleotide.

An additional aspect of the present invention relates to a method for characterizing a sample, consisting in hybridizing the DNA fragments obtained using a method as described above to one or more nucleic sequences of DNA, RNA or PNA type carried on a solid support, and in visualizing the signal emitted by the hybridized fragment (s). Preferably, the solid support can be a DNA, RNA or PNA chip, a microplate or a film, for example a nitrocellulose film.

Some of these detection techniques are described in detail in particular in [Running (1990) BioTechniques, 8, 276–277], [Kawai (1993) Anal Biochem, 209, 63–69], quantitative [Berndt (1995) Anal Biochem, 225, 252–257], [Winn-Deen (1993) Mol. Cell. Probes, 7, 179 186] and [Cros (1992) Lancet, 340, 870–873], incorporated into the description by way of reference.

Another aspect of the invention relates to a detection kit making it possible to implement the method described above. This kit can in particular comprise homopolymeric oligonucleotides, a terminal transferase, the P1 nuclease, buffers and/or the compounds required for the various reactions, and/or specific probes allowing the detection of the molecules sought. For this purpose, the kit can also comprise DNA, RNA or PNA chips allowing said detection. The agents which may be part of the composition of the kit according to the invention are explained in greater detail in the examples given hereinafter.

The present invention is also directed toward the use of the method or of the kit as mentioned above, for identifying a product, a substance and/or a material, in unmodified form or which has undergone treatments, transformations and/or conditioning, or for identifying its origin and/or its family. For example, this method or the kit allows the detection of the presence of genetically modified organisms (GMOs) or of traces of GMO in a sample.

The method or kit according to the invention also allows the identification and/or the quantification of contaminants in a product, a substance and/or a material, in unmodified form or which has undergone treatments, transformations and/or conditioning.

For example, the product can originate from the human or animal body; it can be a human secretion, possibly in trace amounts. The product perhaps a plant or animal, possibly transgenic animal, extract. In this situation, the method of the invention makes it possible to rapidly detect the presence of transgenes.

Advantageously, the product perhaps an agro-foods or pharmaceutical product, and the contaminant a microorganism such as a bacterium, a virus or a fungus.

For the remainder of the description, reference will be made to the legends of the figures given hereinafter.

LEGENDS

Figure 1B:
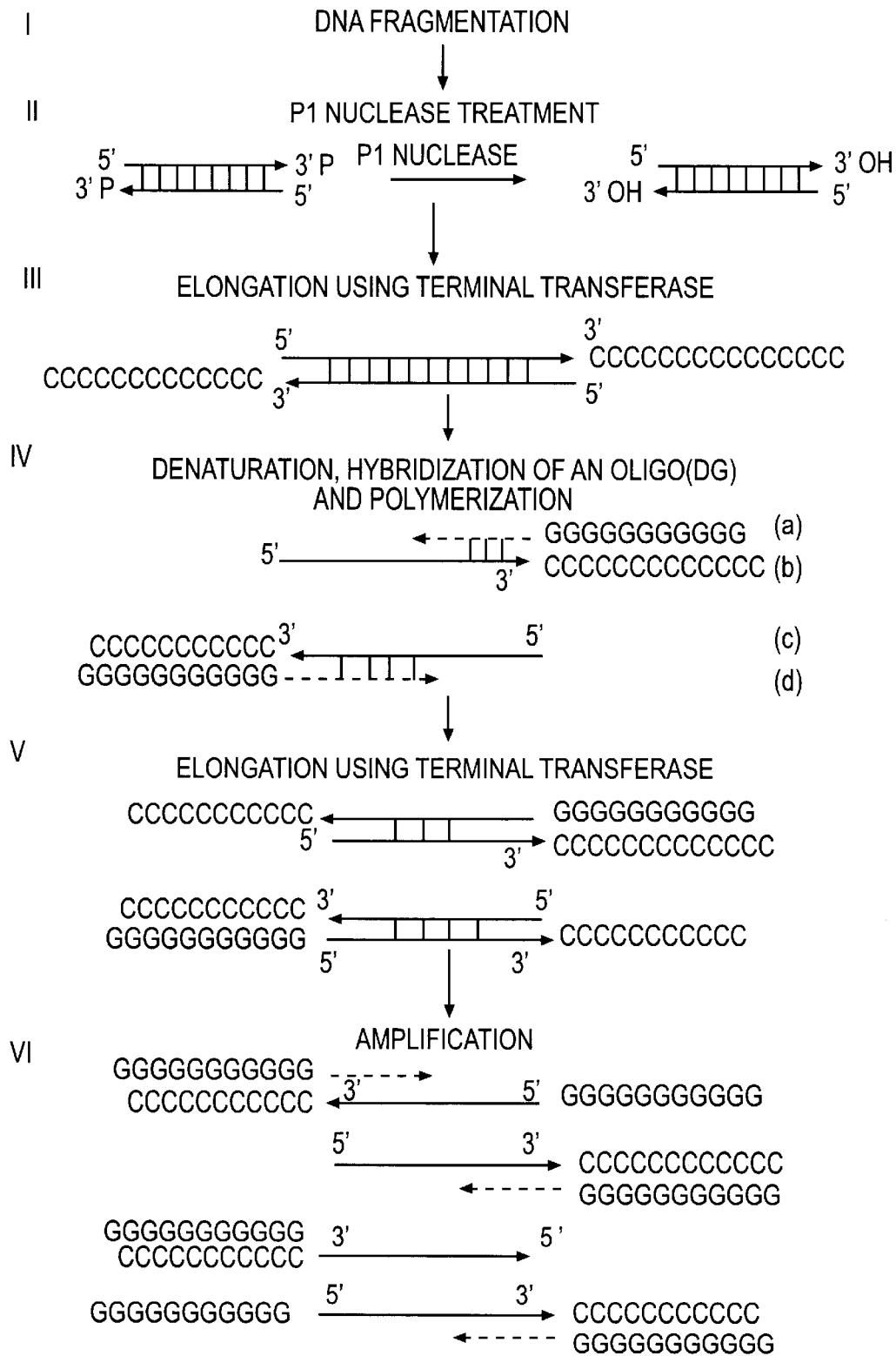

FIGS. 1A and 1B: schematic representations of the method according to the invention The arrows in thick lines indicate the two strands, in opposite directions, of the DNA. The small vertical lines indicate that the two strands are paired. 5' and 3' define the ends of the DNA according to the nomenclature. The Cs represent the addition of deoxycytidine-5'monophosphate (the number of Cs added is not a parameter upon which the success of the amplification closely depends). The C:G pairing is not associated with small vertical lines, this pairing being known to those skilled in the art. The steps V in FIGS. 1A and 1B achieve the same result, namely allowing the amplification in the subsequent steps. This step therefore consists either of denaturation-slow renaturation, or of the addition of a poly(dC) oligonucleotide to the 3' ends of the DNA fragments using terminal transferase activity.

Figure 2A:
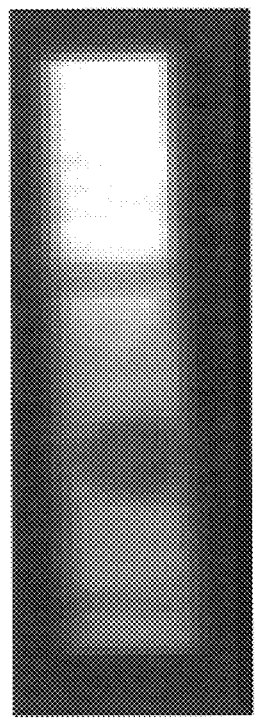
Figure 2B:
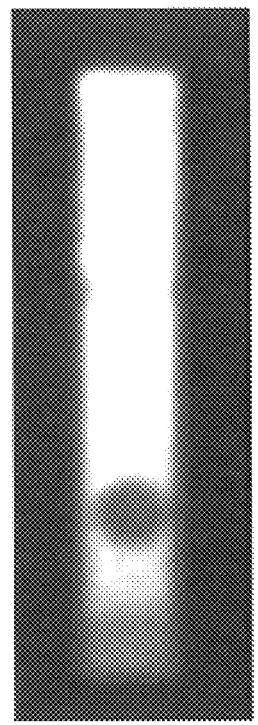

FIGS. 2A and 2B: demonstration of the terminal transferase activity.
  A. Soybean genomic DNA fragmented by sonication and elongated using terminal transferase.
  B. Soybean genomic DNA fragmented by enzymatic digestion and elongated using terminal transferase.

Figure 3:
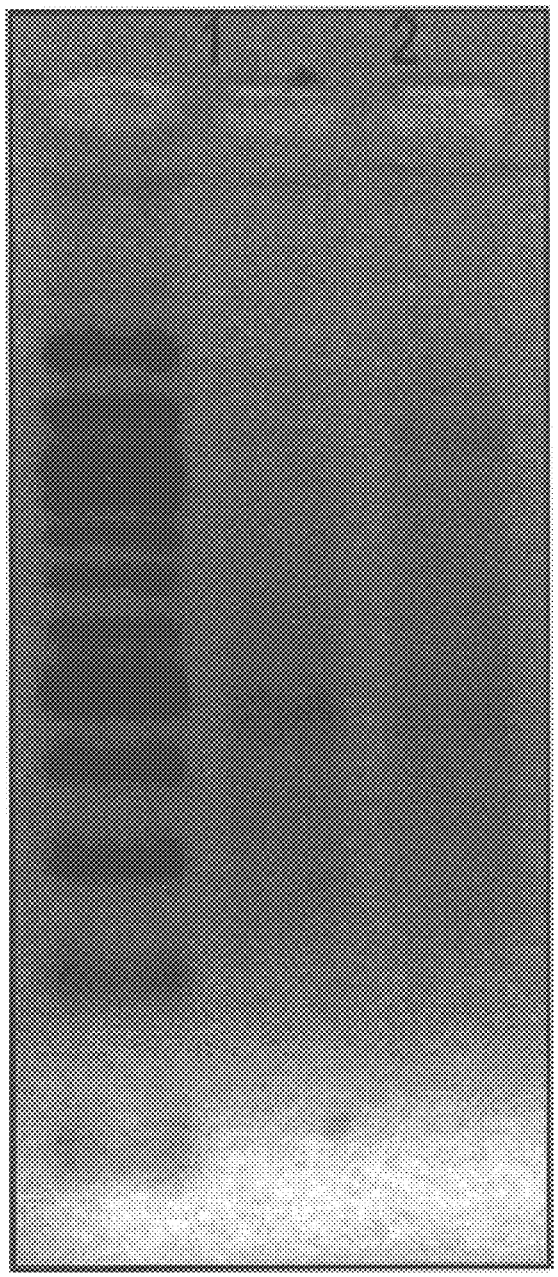

FIG. 3: revelation by 2% agarose gel electrophoresis of the amplification products obtained after denaturation and renaturation of the elongated DNAs.
  A. Soybean genomic DNA fragmented by sonication.
  B. Soybean genomic DNA fragmented by enzymatic digestion.

Figure 4:
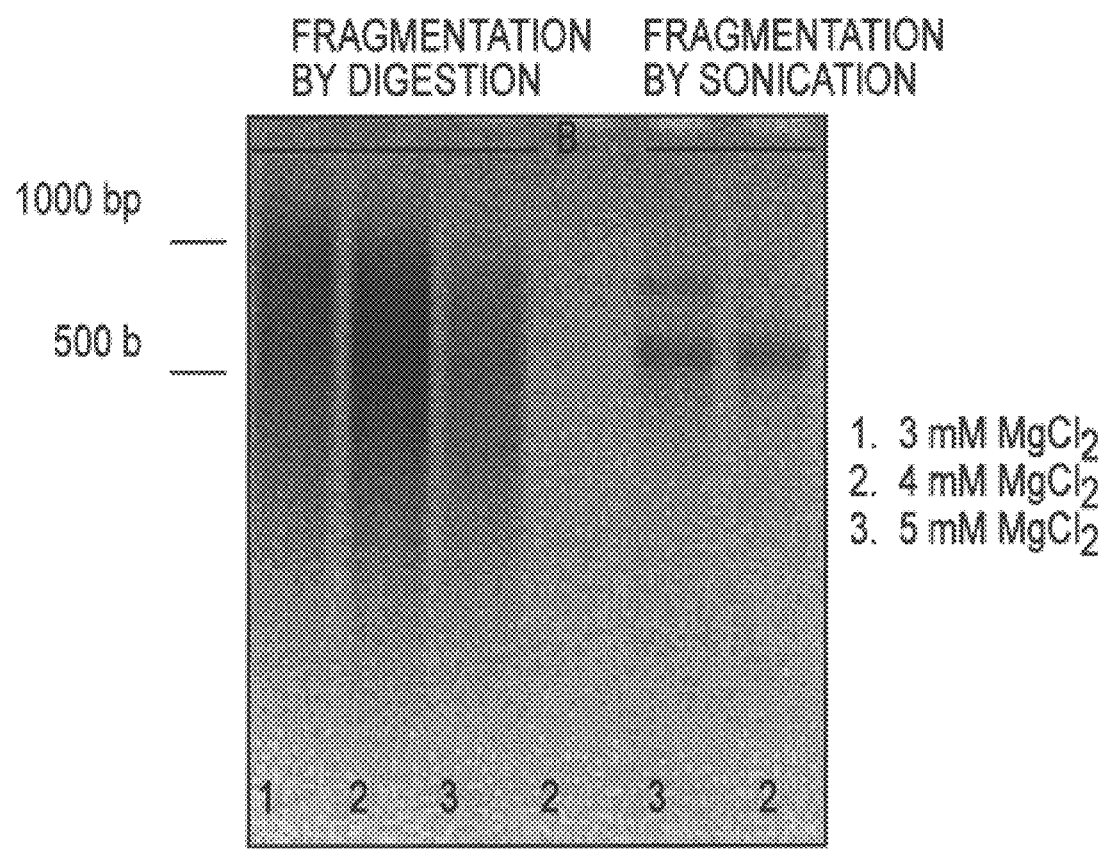

FIG. 4: revelation by 2% agarose gel electrophoresis of the amplification products obtained after 2 terminal transferase steps.

Figure 5:
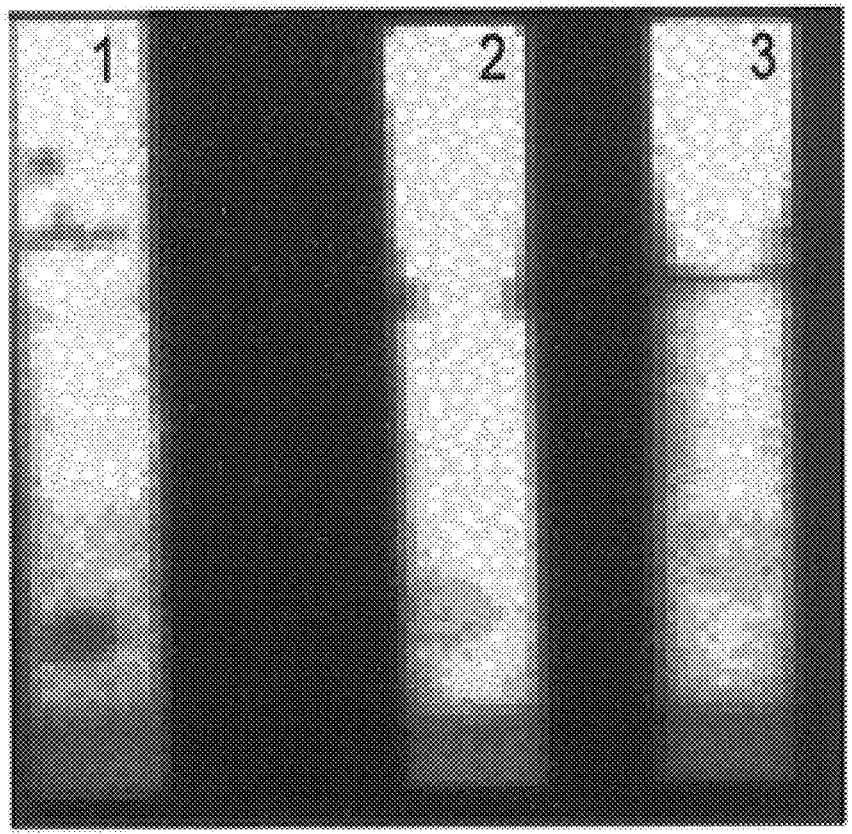

FIG. 5: universal amplification of genomic DNA. Revelation by hybridization of the PCR products obtained after denaturation/renaturation (1) or 2 terminal transferase steps (2 and 3)
  probe specific for a constitutive soybean gene 2 and 3. two probes specific for 2 constitutive soybean genes

DETAILED DESCRIPTION

The method according to the invention consists in adding, to all the DNA fragments contained in a sample, a chain consisting of a single type of nucleotide, at the 3' end of this DNA. This series of nucleotides can be used directly for detection, after hybridization to the capture probes carried by the chip, or be used in a subsequent basic step common to all the fragments for labeling or amplification.

The enzyme preferably used is terminal transferase (EC 27731; enzyme extracted in particular from calf thymus, also termed terminal deoxynucleotidyl transferase). This enzyme has the property of catalyzing, independently of the DNA sequence, the addition of deoxyribonucleoside triphosphates ("dNTPs") to the 3'-hydroxy (3'OH) ends of single- or double-stranded DNA. Thus, for example, the incubation of DNA with terminal transferase, in the presence of deoxycytidine triphosphate (dCTP), will lead to the synthesis, at the two 3'OH ends of all the DNA fragments, of a poly(dC) chain. Under suitable conditions, this type of labeling has, in particular, the advantage of labeling all the DNA molecules uniformly and, therefore, of not introducing any bias into the relative representativeness of all the DNA molecules.

The fact that the DNA may have undergone treatment having cleaved it such that 3'-phosphate (3'P) ends have been generated is taken into consideration. In this case, the addition of dNTPs to the ends of the DNA using terminal transferase is not possible. In an advantageous method according to the invention, the DNA is pretreated using the P1 nuclease (EC 31301, enzyme extracted in particular from Penicillium citrinum), which has, in particular, a 3'-nucleotidase activity which removes the 3'-phosphates from the DNA so as to generate 3'-hydroxy (3'OH) ends. Thus, all the DNA fragments treated will potentially be substrates for terminal transferase.

The nucleotides incorporated using terminal transferase can be labeled so as to be detected by conventional techniques, such as the use of enzymes capable of acting on a chromogenic, fluorigenic or luminescent substrate (at least one of the primers used in the PCR is, for example, biotinylated, and the detection of the hybridization is carried out by adding streptavidin coupled to an enzyme such as peroxidase and then a chromogenic substrate for the enzyme), radioactivity, fluorescence or electrochemiluminescence. Thus, such fragments, hybridized to the chip, will be identified, the hybridization of the DNA via the target sequence providing the specificity of hybridization, and the labeled-dNTP elongation allowing the detection at the site of hybridization. This implementation is dependent on the sensitivity of detection of the chip system and on the starting amount of DNA.

One of the remarkable aspects of the invention is the fact that the elongation is used as a site of annealing with a polymerization primer complementary to the elongation sequence and common to all the DNA fragments. For example, following a poly(dC) elongation, a poly(dG) polymerization primer will be used.

In such an advantageous method, the polymerization primer can be labeled for detecting the hybridization of the newly synthesized DNA strand or alternatively, a labeled nucleotide will be incorporated during the polymerization, for detecting the hybridization of the newly synthesized DNA strand. The incorporation of the labeled nucleotide is carried out in a single step of synthesis of the DNA strand, a copy of the matrix DNA, using the primer complementary to the terminal transferase dNTP elongation, through the action of any DNA polymerase having the required enzymatic activity. The incorporation of the labeled nucleotide can also be carried out during a series of steps of synthesis of the DNA strand, a copy of the matrix DNA, using the primer complementary to the terminal transferase DNTP elongation. This labeling can therefore be carried out directly during the method according to the invention.

The oligonucleotide complementary to the elongation can, in addition to the series of the same base, comprise, at its 5' end, a sequence which is not complementary to the elongation sequence and which, during the PCR polymerization steps, will reconstitute a double-stranded sequence recognized by a restriction enzyme. Although this is not necessary, the presence of a restriction site, preferably generating sticky ends, may facilitate cloning of the amplified sequences.

The product generated is then hybridized to a nucleic acid sequence of DNA, RNA or PNA (Peptide Nucleic Acid) type, carried on any type of support, preferably of DNA chip, or even microplate, type, and the signal generated by the possible hybridization is measured by any possible technique.

In the agro-foods domain, the method of the invention concerns, inter alia, starting products such as meat and vegetables (or products derived from vegetables in all their forms), intermediate products and finished products. In other domains, such as that of pharmacy, this concerns in particular lecithin, glucose syrup and fermentation products.

EXAMPLE 1

Single-primer amplification of all the DNA of a Sample Derived from Several Genomes, after a Denaturation, Slow Renaturation Step This example is illustrated in FIG. 1A.

The starting DNA is a mixture of DNA: soybean DNA, maize DNA and human DNA.

$1^{st}$ step: since the procedure applies only to DNAs which are small in size, the various DNAs are fragmented.

Two fragmentation techniques are used: either sonication, which gives fragments which are less than 500 bp in size, or digestion with a restriction enzyme which cleaves the DNA with a relatively high frequency and which produces blunt ends (AluI or HaeIII type). This technique gives smaller fragments (around 250 bp).

$2^{nd}$ step: the sonication cleaves the DNA randomly and thus produces 3'OH ends and 3'P ends. The terminal transferase allows nucleotides to be added only to the 3'OH ends of a DNA, the ends of the sonicated DNA are made 3'OH through the action of the P1 nuclease.

When the DNA is fragmented with restriction enzymes, the ends are 3'OH.

$3^{rd}$ step: a homopolymeric sequence is added to the 3' end of the DNAs using the terminal transferase. For this, the DNA is mixed together with 120 U of terminal transferase and 250 $\mu$M of dCTP, and incubated for 15 minutes at 37° C.

The DNA is then purified on silica resin (PCR qiaquick purification kit from Qiagen). The elongation is verified by hybridization on a nitrocellulose strip. The elongated DNA is fixed, with UV light, on the nitrocellulose membrane, and then a biotinylated homopolymeric primer (in this case, polydG, the number of dG being 11, which will subsequently be termed dG11) is brought into contact with the strip and migrates over the strip by capillary action. Colorimetric revelation of the biotin appears at the fixed DNA if this DNA is elongated (FIG. 2). Under the elongation conditions used, it is estimated that about fifteen dCTPs have been incorporated by the terminal transferase.

The DNA obtained is represented in FIG. 1A, III.

$4^{th}$ step: a 5 minute incubation at 95° C. makes it possible to denature the DNA obtained after elongation; the dG1 1 homopolymeric primer can then hybridize to the homopolymeric tail previously added, and a DNA polymerase allows the synthesis of the complementary strands. The DNA obtained (FIG. 1A, IV) cannot be amplified for instance by PCR.

$5^{th}$ step: denaturation (S minutes at 95° C.) followed by slow renaturation (drop from 95° C. to 35° C. with a ramp of 0.2° C. per second) allows re-annealing of the DNA strands and the formation of DNA molecules which can be amplified by PCR (FIG. 1A, V).

$6^{th}$ step: after synthesis of the complementary strands and denaturation, the DNA can be amplified exponentially by PCR (FIG. 1A, VI) under the following conditions:

1×incubation buffer, 200 µM dNTPs, 1 µM dG11 oligonucleotide, 3 mM MgCl$_2$, 2 U Taq DNA polymerase amplification cycles: 95° C. 30 sec/50° C. 2 min/72° C. 1 min, 60 cycles Thermocycler: Minicycler from MJ Research Steps 4 to 6 are also carried out using a pulsed-air thermocycler (LightCycler from Roche). For this, the DNA is incubated in the presence of 2 µl of DNA Master SYBR GREEN (Roche Boeringher), 0.16 µl of anti-Taq antibodies (Clontech), 5 mM MgCl$_2$ and 1 µM of dG11 primer.

The DNA is then subjected to the following cycles a denaturation phase (2 minutes at 95° C.)

a first PCR cycle (95° C. 2 sec, 50° C. 15 sec. 72° C. 28 sec)

a new denaturation (2 minutes at 95° C.) followed by slow renaturation (from 95° C. to 35° C. with a ramp of 0.2° C./sec) and 60 PCR cycles (95° C. 2 sec, 50° C. 15 sec, 72° C. 28 sec).

Two methods for analyzing the result were used:

Firstly, the amplified DNA is subjected to 2% agarose gel electrophoresis (FIG. 3).

Secondly, the amplification is verified by hybridization on a nitrocellulose strip.

For this, the amplification is carried out with a biotinylated dG11 oligonucleotide. A probe characteristic of the mixture analyzed is deposited onto a nitrocellulose strip and fixed with UV light. The PCR product obtained after amplification is denatured and migrates over the nitrocellulose strip by capillary action. If the amplicon contains the sequence complementary to the probe, a colorimetric reaction forms at the probe due to the revelation of the biotin. These results are illustrated in FIG. 5.

EXAMPLE 2

Single-primer Amplification of all the DNA of a Sample Derived from Several Genomes and Modified using Two Terminal Transferase Steps This example is illustrated in FIG. 1B.

In this example, the starting DNA is the same as in the previous example.

$1^{st}$ and $2^{nd}$ steps: the fragmentation and P1 nuclease treatment steps, if necessary, are identical to those of Example 2.

$3^{rd}$ step: a homopolymeric sequence (in this case, polydc) is added to the 3' end of this DNA and will be used for anchoring a universal primer.

For this, the DNA is incubated for 15 minutes at 37° C., in the presence of 120 U of terminal transferase and 250 µM of dCTP, and then purified on silica resin (PCR qiaquick purification kit from Qiagen). The elongation is verified by hybridization on a nitrocellulose strip. The elongated DNA is fixed, with UV light, on the nitrocellulose membrane, and then a biotinylated homopolymeric primer (in this case, polydG, the number of dG being 11) is brought into contact with the strip and migrates over the strip by capillary action. A revelation of the biotin appears at the fixed DNA if this DNA is elongated (FIG. 2). Under the elongation conditions used, it is estimated that about fifteen dCTPs have been incorporated by the terminal transferase.

$4^{th}$ step: the elongated DNA is then denatured and a primer complementary to the added homopolymeric sequence (in this case, a dG11 primer) is hybridized to the denatured DNA. A DNA polymerase (in this case, Taq DNA polymerase) is added in order to synthesize the complementary strand. The DNA obtained is represented in FIG. 1B, IV.

$5^{th}$ step: a second terminal transferase step, performed under the same conditions as the first, is carried out on the elongated DNA and thus makes it possible to have a DNA with a homopolymeric sequence (in this case, polydC) at the 2 ends of the DNA. This DNA is subjected to denaturation and then hybridization with a dG11 oligo, and polymerization of the complementary strand in the presence of a DNA polymerase. The DNA obtained is represented in FIG. 1B, V.

Denaturation followed by the hybridization of the dG11 oligonucleotide and by synthesis of complementary strand using a DNA polymerase makes it possible to obtain a DNA which can be directly amplified by PCR with a homopolymeric primer (in this case, a dG11) (FIG. 1B, VI).

$6^{th}$ step: this amplification is carried out on a minicycler thermocycler from MJ Research, under the following conditions:

15×incubation buffer, 200 µM dNTPs, 1 µM dG11 oligonucleotide, 3 mM MgCl$_2$, 2 U Taq DNA polymerase amplification cycles: 95° C. 30 sec/50° C. 2 min/72° C. 1 min, 60 cycles.

The $6^{th}$ step was also carried out on a pulsed-air thermocycler (LightCycler from Roche).

For this, the DNA is incubated in the presence of 2 µl of DNA Master SYBR GREEN (Roche Boeringher), 0.16 µl of anti-Taq antibodies (Clontech), 5 mM MgCl$_2$ and 1 µM of dG11 primer.

The DNA is then subjected to denaturation (2 minutes at 95° C.), and then to 60 PCR cycles (95° C. 2 sec, 50° C. 15 sec, 72° C. 28 sec).

Two methods for analyzing the result were used:

Firstly, the amplified DNA is subjected to 2% agarose gel electrophoresis (FIG. 4).

Secondly, the amplification is verified by hybridization on a nitrocellulose strip.

For this, the amplification is carried out with a biotinylated dG11 oligonucleotide. A probe characteristic of the mixture analyzed is deposited onto a nitrocellulose strip and fixed with UV light. The PCR product obtained after amplification is denatured and migrates over the nitrocellulose strip by capillary action. If the amplicon contains the sequence complementary to the probe, a violet spot forms at the probe due to the calorimetric revelation of the biotin. These results are illustrated in FIG. 5.

EXAMPLE 3

Pre-amplification for the Detection on a Solid Support (a DNA Chip, for Example)

Step 1: The DNA, extracted from the sample taken from a food product, is reduced to fragments with a mean size of approximately 200 base pairs, by passing the solution through a needle (the number of times the DNA solution is passed through the needle and the diameter of the needle are two parameters which define the mean size of the DNA by causing random cleavage of the DNA).

Since the cleavage of the DNA could have generated in particular 3'OH ends, but also 3'P ends, the DNA is then subjected to the action of the P1 nuclease (EC 31301), which will remove the possible phosphates at the 3' ends, thus generating 3'OH ends.

Step 2: The DNA is then subjected, for a specific period of time, to a defined amount of terminal transferase (EC 27231), in the presence of a deoxyribonucleotide triphosphate (dCTP), the effect of which is to add a deoxyribonucleotide monophosphate chain to the ends.

Step 3: The DNA is then heat-denatured, preferably at a temperature close to 100° C., in the presence of an oligonucleotide of sequence complementary to the polydc chain added in step 2, and left to cool so as to allow the annealing of a poly(dG) oligonucleotide (oligod(G)).

Step 4: The oligonucleotide will be used as a primer for synthesis, from the 2 ends of the DNA fragments, and the nucleotide sequence of the matrix strands of the DNA will be synthesized using a DNA polymerase, in the presence of the 4 dNTPs. At this stage, labeling of the DNA is introduced using labeled nucleotides.

Step 5: The DNA is once again denatured, and then slowly renatured, the effect of which is annealing of the newly synthesized complementary strands carrying a 5'-protruding oligo(dG) end.

Step 6: These 5' protruding ends are then filled in by the action of a polymerase, in the presence of dCTP. The entire process can be stopped at this stage, but in this example, the amplification is further continued since the DNA is in trace amounts in the sample.

Step 7: The DNA thus formed is used as a matrix for a PCR-type amplification, using the oligonucleotide used in step 2 (oligo(dG)) as the only primer.

Step 8: The entire process having had the effect of amplifying, by a factor at a minimum greater than 2, all of the DNA of the sample, while also having incorporated a label into this DNA, this DNA is then denatured and specific sequences are sought by hybridization to a capture probe fixed to a DNA chip (such as the chips sold by Affymetrix, Cis Bio International/LETI). The presence or absence of contamination with a bacterium is thus detected (for example, the bacterium of botulism, using capture probes specific for this bacteria).

EXAMPLE 4

Aspecific Pre-amplification and Specific Amplification

All of the aspecific amplification products undergo a new specific amplification using specific primers. In this case, the labeling can take place at this stage and the specific amplification products are detected in the same way as described above. More generally, the new amplification can also be carried out using nonspecific primers, of degenerate sequences or of microsatellite-type sequences. The method of the invention is, in this example, a method of preamplification of all of the DNA of the sample, before more specific amplification of sequences of interest. Fragments of sequences in trace amounts can thus be detected, even using samples difficult to analyze

EXAMPLE 5

Quantitative Analysis

Under quantitative PCR conditions (in particular when the number of amplification cycles is such that the amount of each amplification product is proportional to the starting amount of DNA), using the labeled amplification primer, the signal read after hybridization, either on a quantitative PCR machine such as the LightCycler™ (Roche Diagnostics), the Abi Prism $_{7700}$™ (Perkin Elmer) or the icycler™ (Bio-Rad), or on a support allowing quantitative PCR, such as a DNA chip, for example, will make it possible to quantify, absolutely or relatively, according to the conditions, the amount of a specific DNA sequence in the starting sample. The hybridization to a capture oligonucleotide complementary to the oligonucleotide used in the method (or to the nucleotide used in the elongation), according to the orientation of these capture oligonucleotides, allows detection of all of the amplified products, and therefore allows the relative quantification of the specific hybridization of a particular sequence.

What is claimed is:

1. A method for amplifying all DNA fragments of a sample, comprising the following steps:
    (A) extracting the DNA fragments and reducing the size of the DNA fragments extracted by physical or enzymatic cleavage to obtain a mean length of between 100 and 300 bp;
    (B) generating free 3'-OH ends of the DNA fragments with P1 nuclease;
    (C) adding a poly(dX) oligonucleotide to the 3' ends of the DNA fragments using a terminal transferase;
    (D) optionally, denaturing the DNA fragments to single stranded DNA fragments if they are double stranded;
    (E) hybridizing the single stranded DNA fragments to a poly(dY) primer complementary to the poly(dX) of step (C);
    (F) polymerizing a DNA, which can be amplified, using a DNA polymerase in the presence of four dNTPs;
    (G) denaturing the DNA produced in step (F); and
    (H) slowly renaturing complementary strands of the DNA denatured in step (G), which have protruding poly (dY) ends.

2. The method as claimed in claim 1, wherein the DNA obtained in step (F) is amplified, said amplification comprising:
    (A) producing poly(dX) complementary to the protruding poly(dY) ends of the DNA in (H), wherein the poly(dX) is produced optionally in the presence only of dXTP; and
    (B) amplifying by PCR.

3. The method as claimed in claim 1, wherein the DNA fragments obtained in (B) have a mean length of 200 bp.

4. The method as claimed in claim 1, wherein the slow renaturation is carried out by dropping from a temperature of between 85° C. and 105° C. to a temperature of between 45° and 25° C., with a temperature ramp ranging approximately from 0.5° C. to 0.05° C. per second.

5. The method as claimed in claim 1, wherein the poly (dX) or poly (dY) oligonucleotide is labeled with a radioactive, fluorescent, or chemiluminescent group, or with a system allowing revelation by colorimetry.

6. The method as claimed in claim 5, wherein at least one labeled nucleotide is incorporated during one of the synthesis steps.

7. A method for characterizing a sample, consisting of hybridizing the DNA fragments obtained using a method as claimed in claim 5 to one or more nucleic sequences of DNA, RNA or PNA type carried on a solid support, and in visualizing the signal emitted by the hybridized fragments.

8. The method as claimed in claim 7, wherein the solid support is a DNA, RNA, or PNA chip, a microplate or a nitrocellulose film.

9. A kit for amplifying all DNA fragments of a sample comprising homopolymeric oligonucleotides, a terminal transferase, P1 nuclease, buffers, specific probes allowing the detection of the molecules sought, and at least one of DNA, RNA or PNA chips allowing for detection.

10. The method as claimed in claim 1, wherein the sample is an unidentified product, substance or material, in unmodified form or which has undergone at least one of treatments, transformations, and conditioning.

11. The method as claimed in claim 1, wherein the sample comprises a genetically modified organism (GMO) or of traces of a GMO in the sample.

12. The method as claimed in claim 1, further comprising identifying contaminants in the sample.

13. The method as claimed in claim 1, further comprising quantifying contaminants in the sample.

14. The method as claimed in claim 12, further comprising quantifying contaminants in the sample.

15. The method as claimed in claim 12, wherein the sample is a human secretion.

16. The method as claimed in claim 12, wherein the sample is a plant or animal extract.

17. The method as claimed in claim 12, wherein the sample is an agricultural food product or pharmaceutical product.

18. The method as claimed in claim 12, wherein the contaminant is a microorganism.

19. The method of claim 5 wherein the system allowing revelation by colorimetry comprises biotin-streptavidin coupled to an enzyme which reacts with a chromogenic, fluorigenic or luminescent substrate.

20. The method of claim 16, wherein the animal or plant is transgenic.

21. The method as claimed in claim 6, wherein the renaturation is carried out by dropping from a temperature of 95° C. to a temperature of 35° C.

22. The method as claimed in claim 4, wherein the temperature ramp is 0.2° C. per second.

23. The method as claimed in claim 18, wherein the microorganism is a bacterium, a virus, or a fungus.

* * * * *

UNITED STATES PATENT AND TRADEMARK OFFICE
CERTIFICATE OF CORRECTION

PATENT NO.    : 6,605,435 B1
DATED         : August 12, 2003
INVENTOR(S)   : Christian Provot et al.

It is certified that error appears in the above-identified patent and that said Letters Patent is hereby corrected as shown below:

Column 16,
Line 9, "claim 6," should read -- claim 4, --.

Signed and Sealed this

Fourth Day of November, 2003

JAMES E. ROGAN
*Director of the United States Patent and Trademark Office*